United States Patent
Appling

(10) Patent No.: US 7,833,215 B2
(45) Date of Patent: Nov. 16, 2010

(54) CATHETER FLUID LOCK METHOD AND DEVICE

(75) Inventor: William M. Appling, Granville, NY (US)

(73) Assignee: AngioDynamics, Inc., Latham, NY (US)

( * ) Notice: Subject to any disclaimer, the term of this patent is extended or adjusted under 35 U.S.C. 154(b) by 215 days.

(21) Appl. No.: 11/551,529

(22) Filed: Oct. 20, 2006

(65) Prior Publication Data

US 2007/0100298 A1    May 3, 2007

Related U.S. Application Data

(63) Continuation-in-part of application No. 11/056,091, filed on Feb. 10, 2005, now abandoned, which is a continuation of application No. 10/116,299, filed on Apr. 4, 2002, now Pat. No. 6,942,635.

(51) Int. Cl.
*A61M 31/00* (2006.01)
*A61M 5/32* (2006.01)

(52) U.S. Cl. .................................. 604/506; 604/266

(58) Field of Classification Search ............... 604/509
See application file for complete search history.

(56) References Cited

U.S. PATENT DOCUMENTS

| | | | |
|---|---|---|---|
| 4,134,402 A | 1/1979 | Mahurkar | |
| 5,053,004 A | 10/1991 | Markel et al. | |
| 5,053,023 A | 10/1991 | Martin | |
| 5,209,723 A | 5/1993 | Twardowski et al. | |
| 5,360,397 A | 11/1994 | Pinchuk | |
| 5,558,634 A * | 9/1996 | Mitchell | 604/35 |
| 5,718,692 A | 2/1998 | Schon et al. | |
| 5,800,384 A * | 9/1998 | Russell et al. | 604/43 |
| 5,807,311 A | 9/1998 | Palestrant | |
| 5,947,953 A | 9/1999 | Ash et al. | |

(Continued)

OTHER PUBLICATIONS

Betjes et al., "Prevention of Dialysis Catheter-Related Sepsis with a Citrate-Taurolidine-Containing Lock Solution", *Nephrol. Dial. Transplant.*, 19(6): 1546-51 (2004).

(Continued)

*Primary Examiner*—Nicholas D Lucchesi
*Assistant Examiner*—Jason Flick
(74) *Attorney, Agent, or Firm*—Tara L. Custer

(57) ABSTRACT

A technique for providing a fluid lock in an indwelling catheter, such as is used in hemo-dialysis; the catheter having an annular lumen surrounding a central lumen. The annular lumen, whether used for infusion or aspiration, has a set of ports which are aligned with each other along a circular circumference so that they intersect a common plane. That common plane is substantially perpendicular to the axis of the annular lumen. The catheter is implanted into a patient's cardio-vascular system. There are substantial down times between the blood cleaning procedures for which the catheter is implanted. Fluid is injected into the annular lumen which displaces any blood in the annular lumen proximal of the set of ports. This fluid is maintained in the annular lumen displacing blood throughout the down time of the catheter thereby providing fluid lock and avoiding blood clot within the annular lumen proximal of the set of ports. The ports in the annular lumen face radially outward to assure that the port edges do not snag on tissue when the catheter is inserted.

22 Claims, 10 Drawing Sheets

U.S. PATENT DOCUMENTS

| | | | |
|---|---|---|---|
| 5,961,485 A * | 10/1999 | Martin | 604/43 |
| 6,001,079 A | 12/1999 | Pourchez | |
| 6,340,355 B1 | 1/2002 | Barrett | |
| 6,461,321 B1 | 10/2002 | Quinn | |
| 6,517,529 B1 | 2/2003 | Quinn | |
| 6,533,763 B1 | 3/2003 | Schneiter | |
| 6,540,714 B1 | 4/2003 | Quinn | |
| 6,814,718 B2 * | 11/2004 | McGuckin et al. | 604/264 |
| 6,942,635 B2 | 9/2005 | Rosenblatt et al. | |
| 2005/0143687 A1 | 6/2005 | Rosenblatt et al. | |

OTHER PUBLICATIONS

Dogra et al., "Pevention of Tunneled Hemodialysis Catheter-Related Infections Using Catheter-Restricted Filling with Gentamicin and Citrate: A Randomized Controlled Study", *J. Am. Soc. Nephrol.* 13:2133-2139 (2002).

Droste et al., "Stability and in vitro Efficacy of Antibiotic-Heparin Lock Solutions Potentially Useful for Treatment of Central Venous Catheter-Related Sepsis", *J. Antimicrob. Chemo.*, 51:849-855 (2003).

Hemmelgarn et al., "Prevention of Catheter Lumen Occlusion with rT-PA Versus Heparin (Pre-CLOT): Study Protocol of a Randomized Trial", *BMC Nephrol.*, 7:8 (2006).

Johnston et al., "Central Venous Catheter-Associated Bloodstream Infections in Hemodialysis Patients: Another Patient Safety Bundle?", *Can. J. Dis. Med. Microbiol.*, vol. 17, No. 2 (Mar./Apr. 2006).

Kim et al., "Prevention of Uncuffed Hemodialysis Catheter-Related Bacteremia Using an Antibiotic Lock Technique: A Prospective, Randomized Clinical Trial", *Kidney Intl.*, 69:161-164 (2006).

* cited by examiner

CATHETER FLUID LOCK METHOD AND DEVICE

REFERENCE TO RELATED APPLICATIONS

This application is a continuation-in-part of application Ser. No. 11/056,091 filed Feb. 10, 2005 now abandoned, entitled: "Blood Treatment Catheter And Method", which application in turn is a continuation of Ser. No. 10/116,299 filed on Apr. 4, 2002 and issued on Sep. 13, 2005 as U.S. Pat. No. 6,942,635 entitled "Blood Treatment Catheter And Method". The entire disclosures of said applications and patent are incorporated herein by reference.

BACKGROUND OF THE INVENTION

This invention relates in general to ensuring fluid lock in an indwelling catheter, for use in the cardiovascular system, such as a hemo-dialysis catheter.

The hemo-dialysis catheter is maintained in the patient between dialysis procedures. In order to avoid blood clot within the catheter, a charge of heparinized saline is placed in the catheter to displace the blood and prevent blood clot. This state is called heparin lock or, more generically, fluid lock. The time between blood cleaning procedures (often called dialysis interval time) generally is two to four days.

In order to avoid infection, an antibiotic solution might be used in the catheter to displace the blood and create a fluid lock. Antibiotic heparin might be employed for the fluid lock to prevent both blood clot and infection during the dialysis interval time.

In a typical catheter having a central aspiration lumen and an annular infusion lumen, the openings near the distal end of the infusion lumen are staggered axially. Accordingly, when the heparinized saline is injected into the annular infusion lumen, one of two things occur that negates the function of the heparinized saline and tends to allow a blood clot to form.

In one situation, the heparinized saline exits from the proximal most port thereby failing to displace the blood distal of that exit port.

In another situation, the heparinized saline may be inserted with sufficient flow speed to displace all of the blood in the annular catheter. However, the patient's blood gradually circulates through the openings in the annular lumen, displacing the heparinized saline allowing a blood clot to develop over the zone between proximal and distal openings in the annular catheter.

The heparinized saline is locked into the lumens and this state is often referred to as heparin lock. A blood clot at the distal zone prevents the heparin lock from performing its anti-clotting function at that zone.

Accordingly, it is an object of this invention to provide a long term indwelling catheter design that maximizes the effect of the heparin lock as well as maximizing the effect of any other fluid lock such as when an antibiotic fluid is used.

It is also important in these catheter designs that the catheter have a smooth surface in order to provide ease of insertion.

BRIEF DESCRIPTION OF THE FIGURES

In FIG. 1, the catheter is inserted into the patient at point A and into the vein at point B.

DEFINITIONS

Infusion and Aspiration Port and Ports

Figure 3:
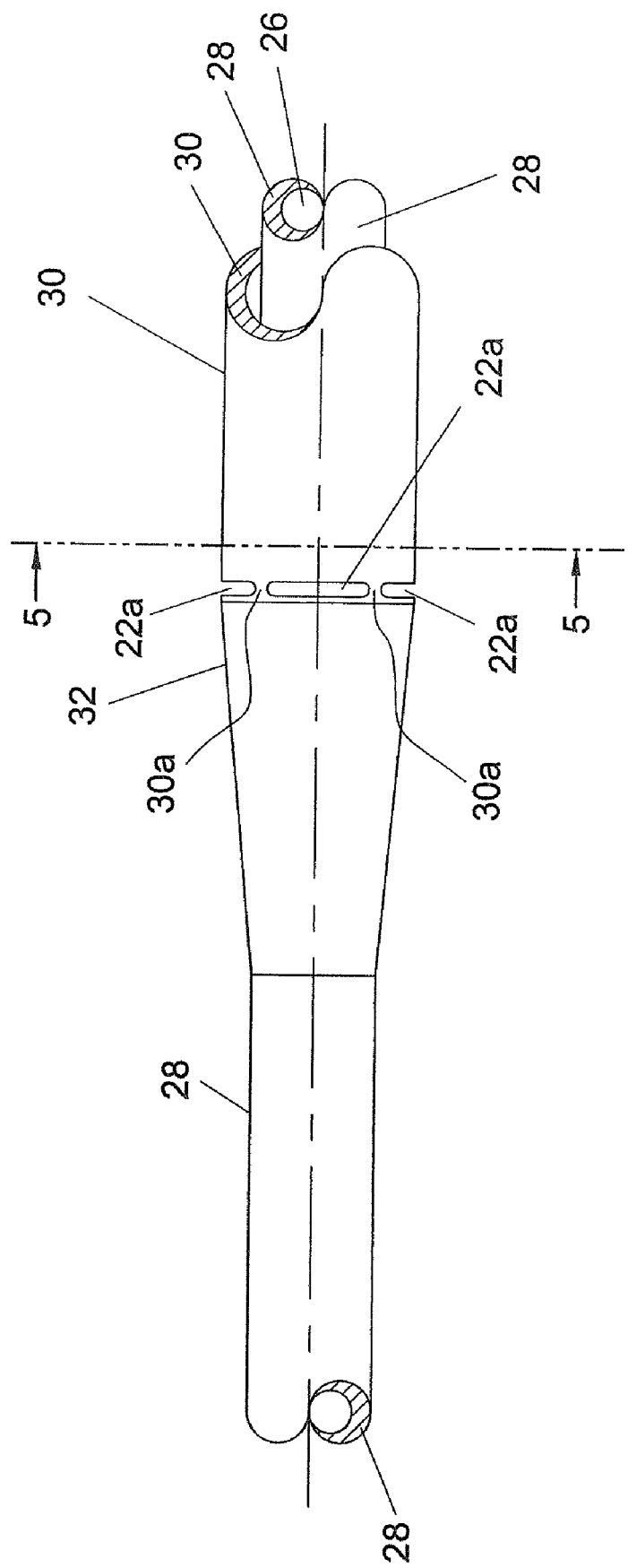
FIG. 3 is an elevation view of the zone around the distal infusion port of a first embodiment of the FIG. 2 catheter showing a plurality of arcuate circumferential ports 22a; all of which intersect a single radial plane.
Figure 6:
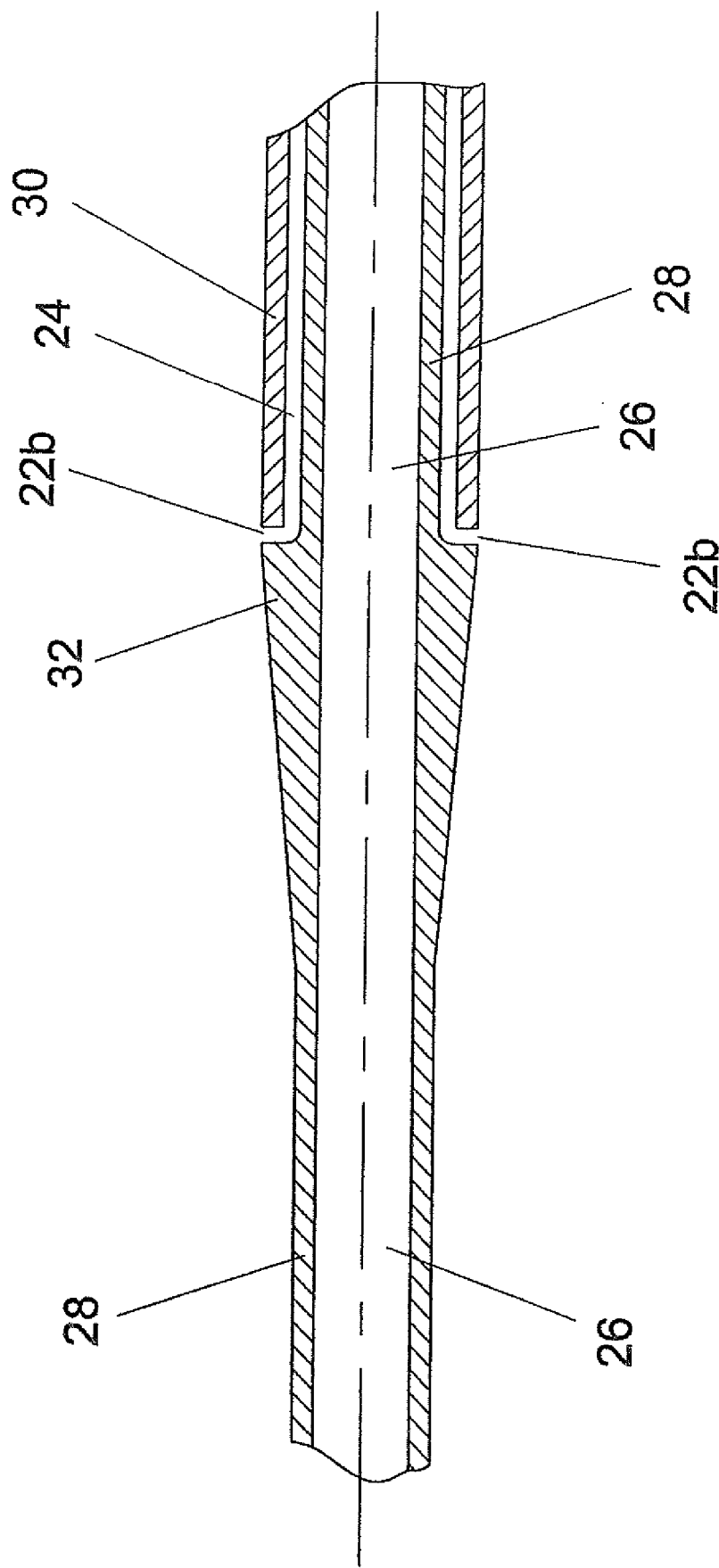
FIG. 6 is a longitudinal sectional view of a second embodiment of the FIG. 2 catheter in which the infusion port arrangement 22 is a circumferential opening 22b interrupted by four radial ribs 34 (see FIG. 8) that support the distal end of the annular infusion tube.
Figure 9:
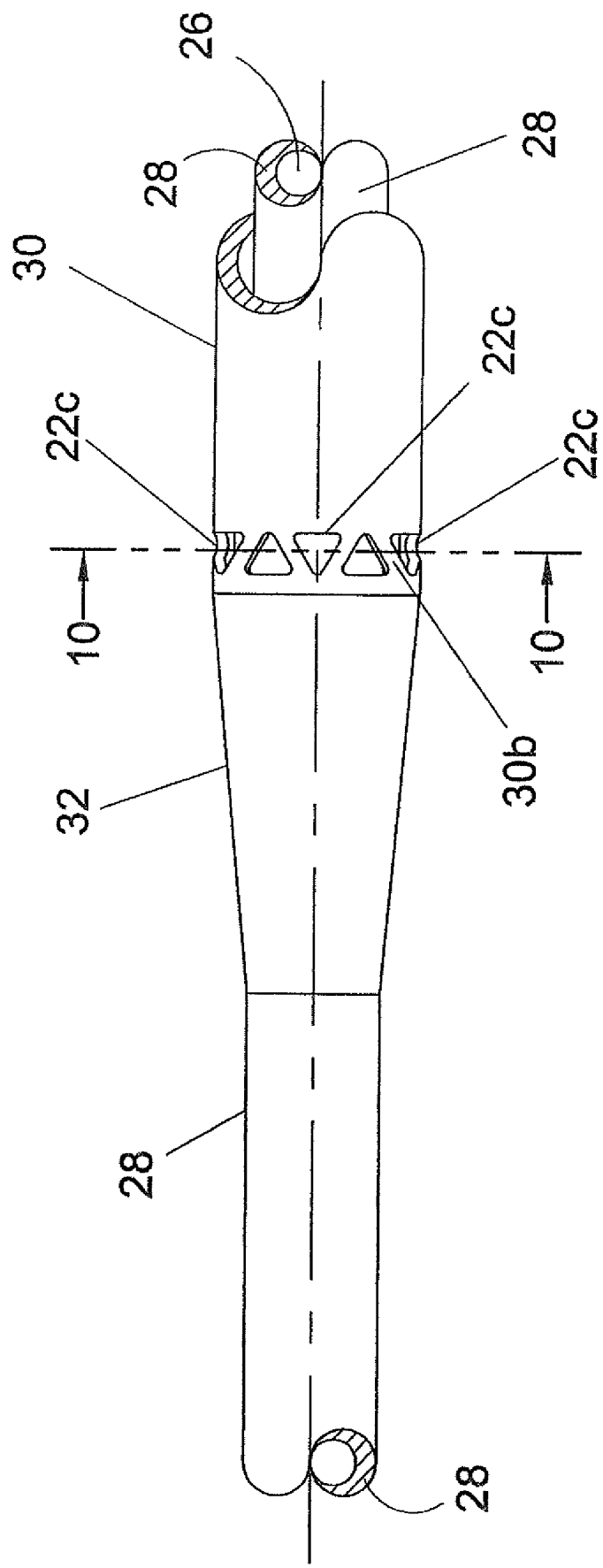
FIG. 9 is an elevational view of a third embodiment showing a set of triangular infusion ports spaced from each other in a nested fashion.

The embodiments shown in FIGS. 3, 6, and 9 contain a plurality of infusion exit ports. A design can be provided in which there is a single circumferential exit port with upstream supports for the annular lumen. The essential feature is that the port or ports all lie along one plane that is substantially perpendicular to the axis of the catheter.

Accordingly, it should be understood that, as applied to either infusion or aspiration lumens, the terms "port" or "ports" or "port arrangement" in the specification and claims are used to include a single port and/or a set of ports.

BRIEF DESCRIPTION

In brief, the catheter disclosed has a shaft with both aspiration and infusion lumens. In the embodiments shown, at a distal zone, the tube carrying the aspiration lumen extends distally of the end of the tube defining the infusion lumen. At its distal end, the infusion lumen is substantially annular, extending around the aspiration tube and has one or more infusion ports that provide emission of fluid all within a single plane.

All of the infusion ports are deployed along a single plane that is substantially perpendicular to the axis of the catheter. This infusion exit port arrangement serves to avoid blood clot during heparin lock in the annular infusion tube.

All of the infusion ports face radially outward to minimize having the port wall edges snag tissue and impede insertion into the catheter.

DESCRIPTION OF THE PREFERRED EMBODIMENTS

Figure 1:
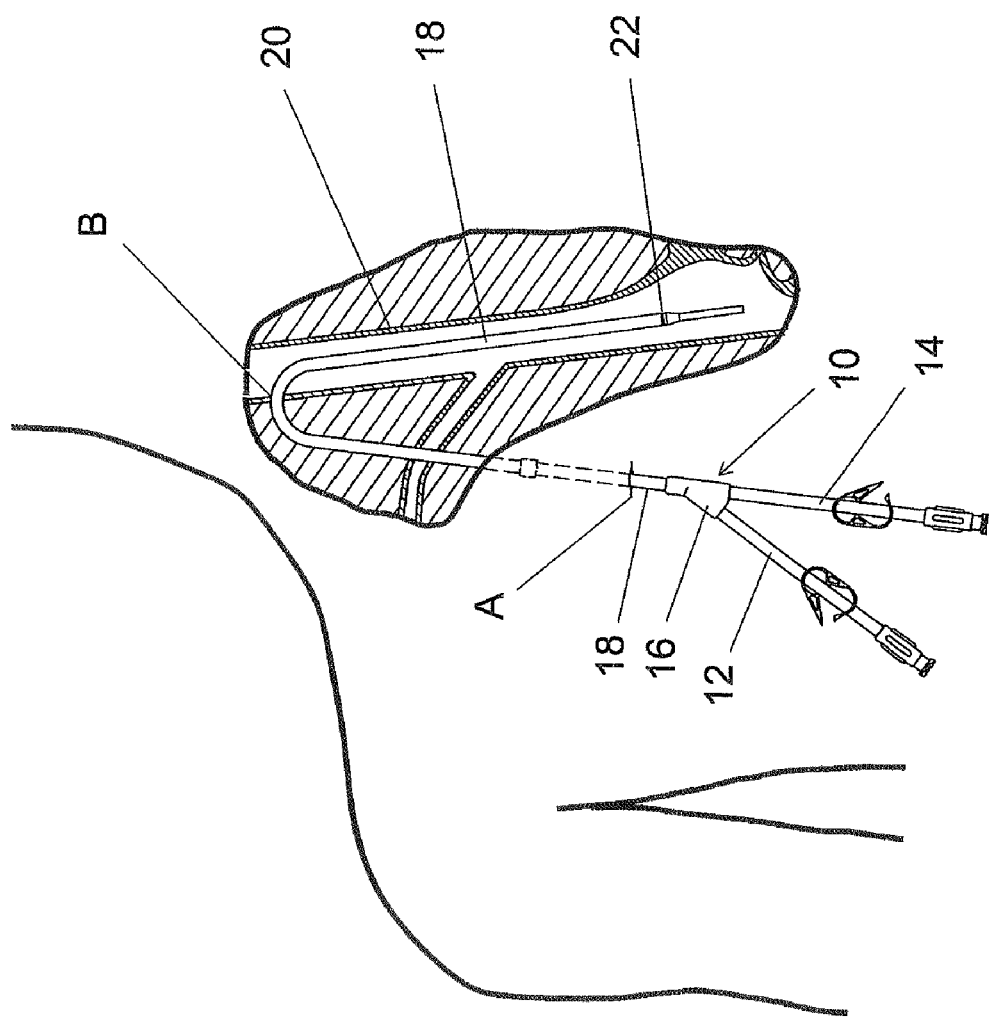
FIG. 1 is a schematic illustration of the positioning of a hemo-dialysis catheter 10 embodiment of this invention through the jugular vein.
Figure 2:
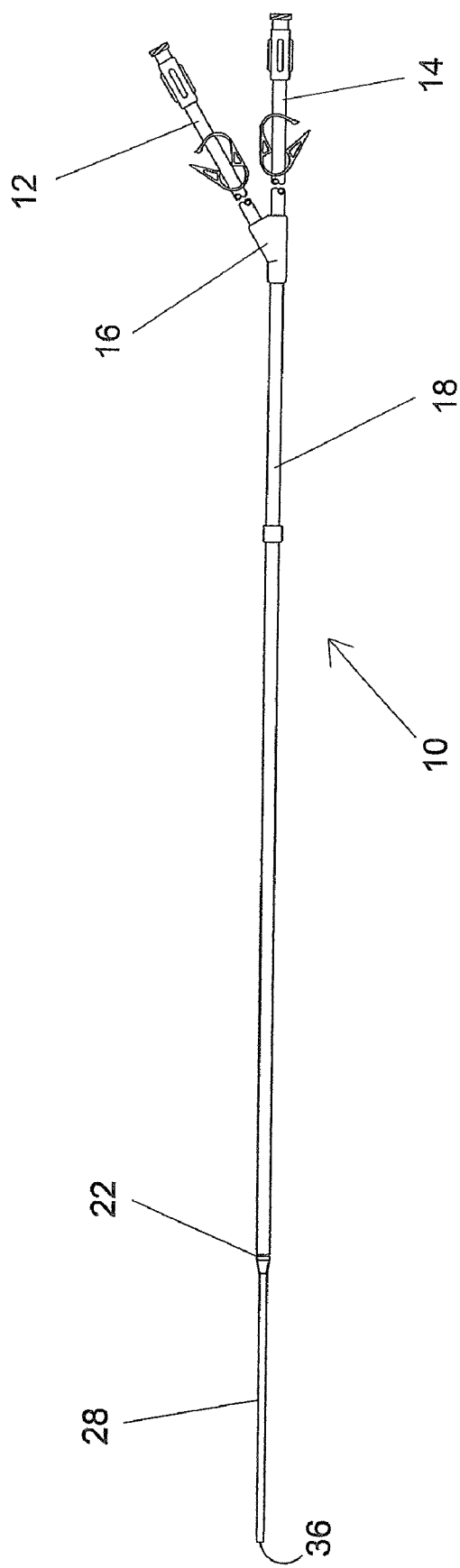
FIG. 2 is an elevation view of an embodiment of the catheter of this invention in which an annular lumen provides infusion and a central lumen provides aspiration. Infusion ports 22 are at the distal end of the annular infusion lumen. An aspiration port 36 is at the distal end of the aspiration lumen.

FIGS. 1 and 2 illustrate the overall design of the catheter 10 embodying the invention.

In particular, a shaft having a standard infusion tube 12 and aspiration tube 14 are combined at a juncture 16 to provide a single shaft 18 distal of the juncture 16. The shaft 18 contains infusion and aspiration lumens. The shaft 18 is inserted into a patient at point A and passed into the jugular vein 20 at point B to be positioned at a desired location; often in the right atrium.

As can be seen in the embodiments shown in FIGS. 3 through 10, the infusion lumen 24 is a circumferential lumen around the aspiration lumen 26 in a zone that is proximal of the infusion exit port arrangement 22. A tubular sidewall 28 defines the aspiration lumen 26. The infusion lumen 24 is defined by tubular sidewall 28 as an inner wall and an outer sidewall 30. The port 22 arrangement is in the outer sidewall 30. The outer sidewall 30 terminates or merges into the sidewall 28 at the built-up zone 32.

Figure 4:
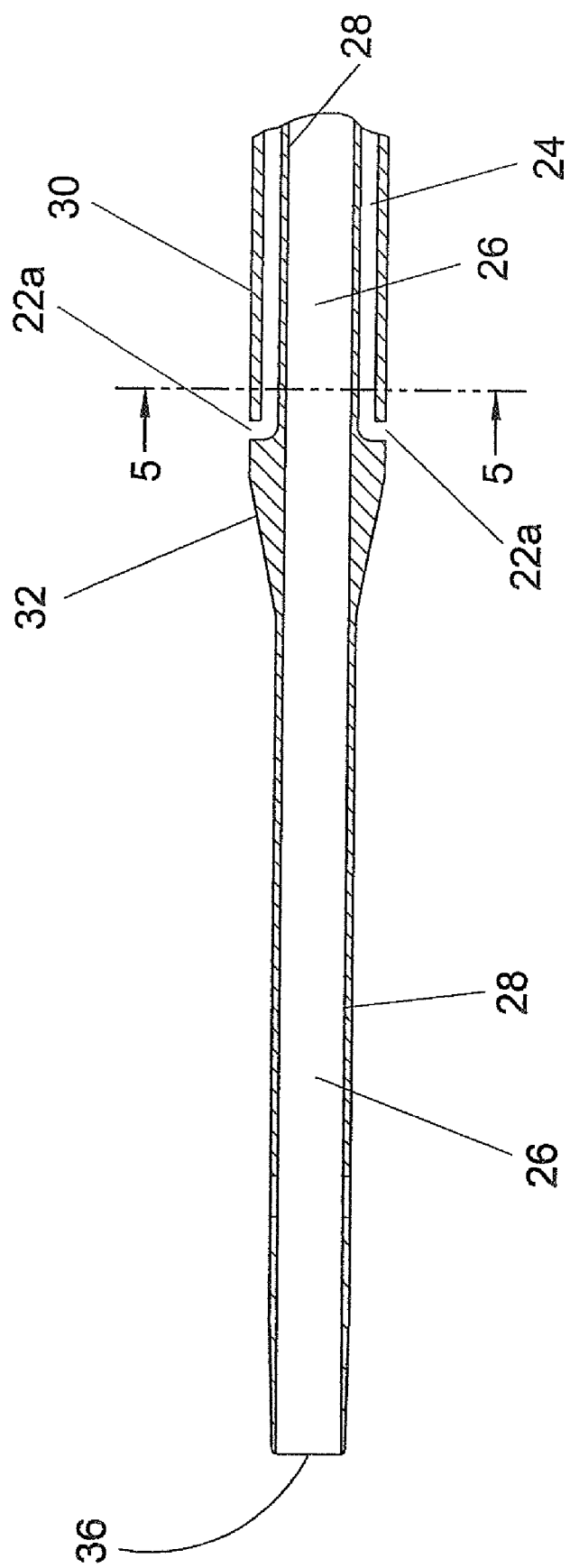
FIG. 4 is a partial longitudinal sectional view along the FIG. 3 catheter portion.
Figure 5:
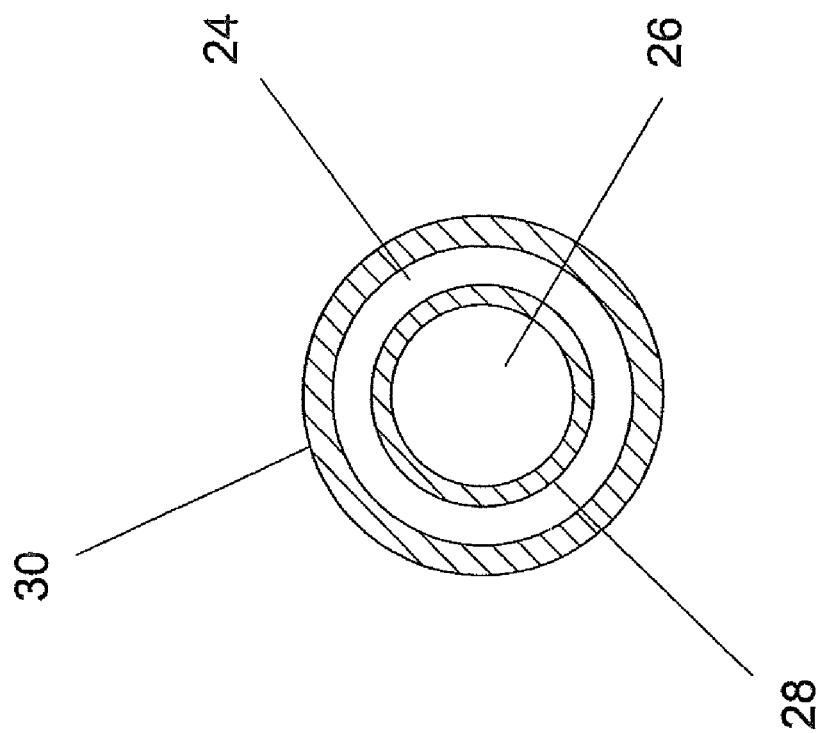
FIG. 5 is a cross-sectional view along the plane 5-5 of FIG. 3.

FIGS. 3 through 5 illustrate a first embodiment of this invention in which the infusion port set 22 is constituted by four circumferential ports 22a separated by small outer wall sections 30a. The port arrangement 22 is at the distal end of the annular infusion lumen 24. The four ports 22a are along a single plane which is substantially perpendicular to the axis of the annular infusion lumen 24. The ports 22a face radially outward and thus the central axis of each port 22a is substantially perpendicular to the axis of the annular infusion lumen 24.

The small outer wall sections 30a merge into the wall 28 at the built-up zone 32. Thus small segments 30a of the outer wall 30 extend through the infusion port zone 22 and define the ports 22a. The approximate dimensions in one embodiment of the openings 22a are 135 mils by 20 mils (0.135 inches by 0.020 inches) and the segments 30b are 25 mils wide.

Figure 7:
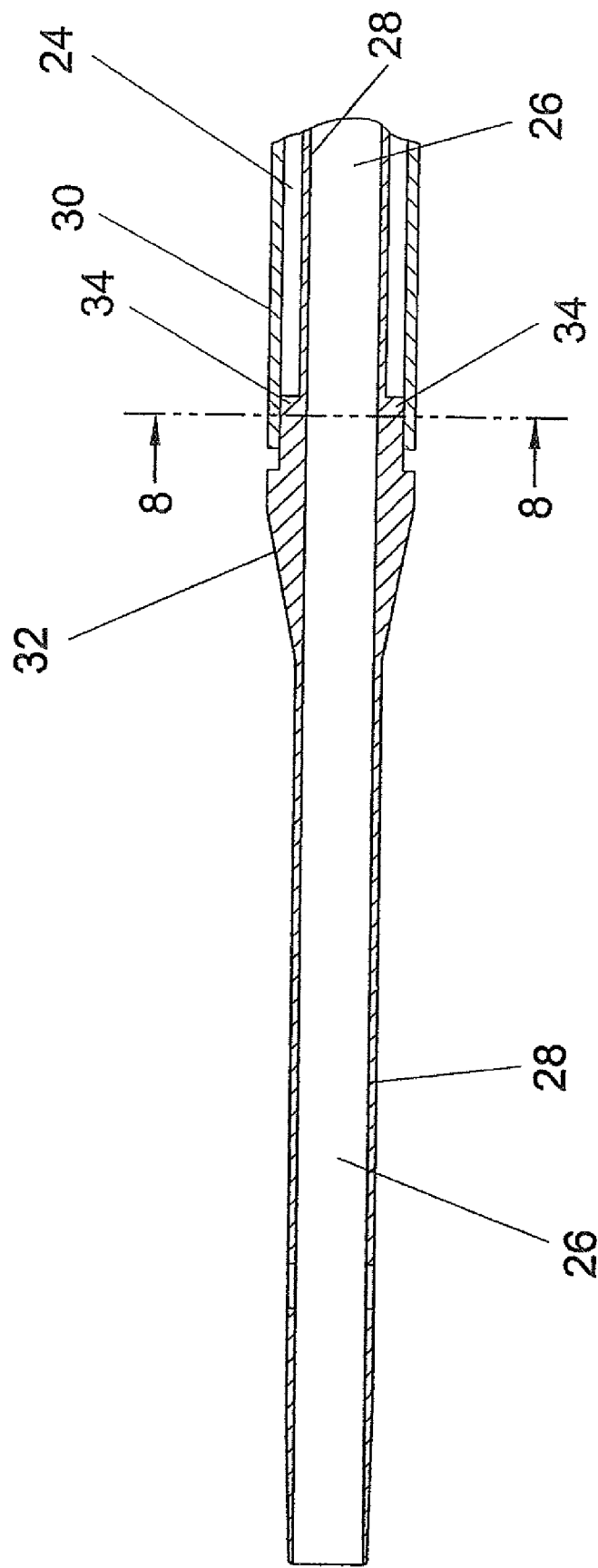
FIG. 7 is a longitudinal sectional view through the ribs 34 of the FIG. 6 catheter.
Figure 8:
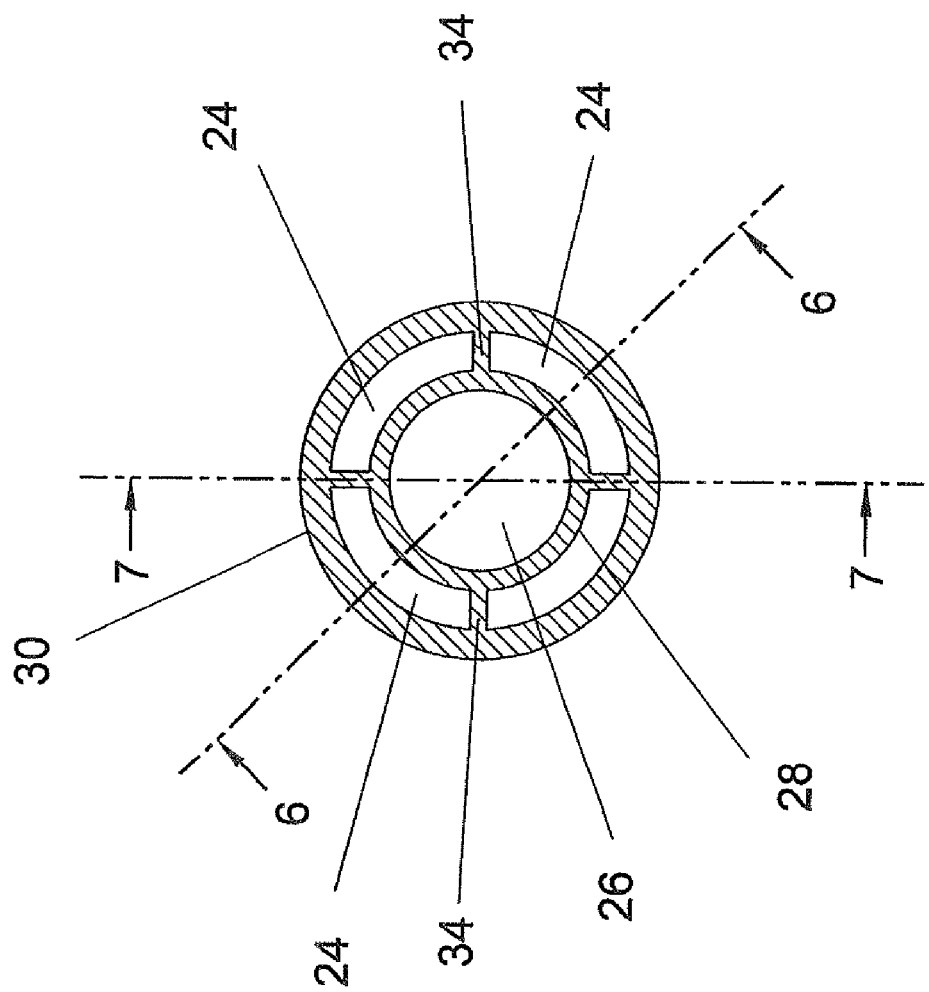
FIG. 8 is a cross-sectional view along the plane 8-8 of FIG. 7 showing the four chamber section of the circumferential infusion lumen immediately adjacent to the four ports that constitute the infusion port arrangement 22b.

FIGS. 6 through 8 illustrate a second embodiment of this invention in which the exit port arrangement 22 are four circumferential ports 22b spaced apart by radial webs 34.

Over a portion of the exit port arrangement 22b, a web design shown in FIG. 8, is employed at the exit ports 22b. This web design assures that the ports 22b are maintained open and prevents the wall 30 from collapsing onto the wall 28. This web design involves four thin webs 34 which extend proximally from the ports 22b for about three millimeters in the embodiment shown.

The web 34 supports are not required in the design shown in FIGS. 3-5. In that design, the outer wall 30 extends past the ports 22a to merge into the wall of the aspiration lumen and thus does not require extra support.

It should be understood that the design of this invention includes an embodiment in which the webs 34 extend the length of the catheter from junction 16 to infusion exit ports 22. Such a design is not presently preferred because it provides a stiffer catheter than do the designs disclosed herein.

Figure 10:
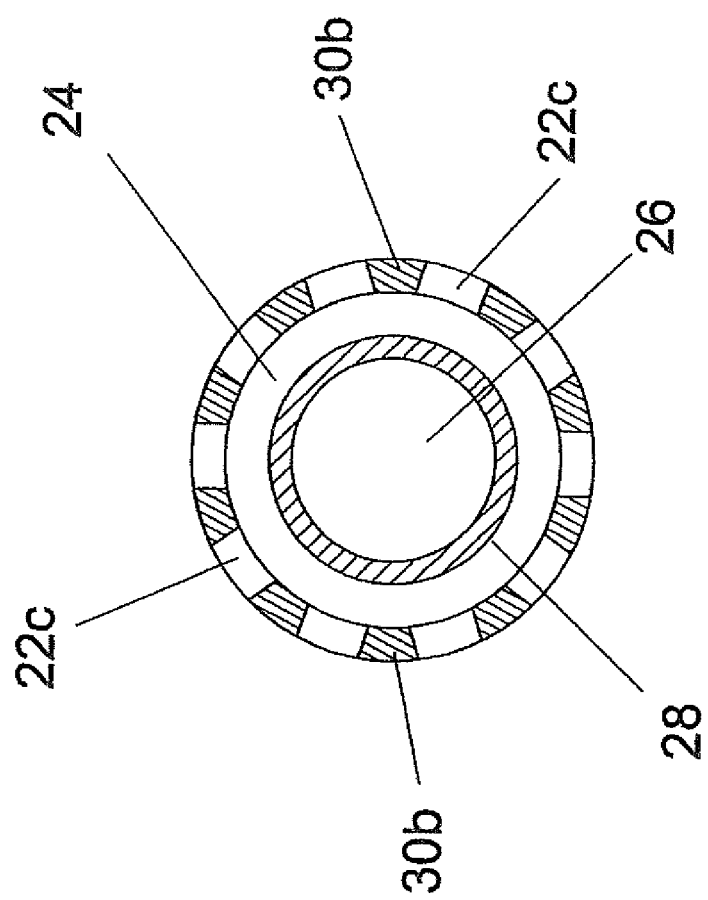
FIG. 10 is a cross-sectional view along the plane 10-10 of the FIG. 9 catheter.

FIGS. 9 and 10 show a third embodiment in which the ports set 22 are a set of triangular ports 22c spaced in a nested fashion next to each other. The ten wall segments 30b provides a sturdy structured support for the distal end of the outer wall 30 while maximizing the cross-sectional area and flow rate of each port.

The design of this invention avoids blood clot development during heparin lock. When the catheter is implanted in a dialysis patient and is not in use, it becomes important to avoid blood clotting in the catheter. This is done by injecting a predetermined amount of heparinized saline into the catheter while the catheter is resident in the patient's body to essentially fill up the interior of the catheter with heparinized saline. The heparinized saline is held or locked into the lumens between dialysis treatment. This is called heparin lock.

In the prior art designs employing co-axial lumens, the outer annular lumen normally has a plurality of openings near the distal end axially displaced from one another. The heparinized saline fills up to the proximal most opening and then exits from that opening and thus fails to fill the space distal of that proximal most opening. A blood clot may form in that space blocking the openings. Alternatively, if the heparinized saline does completely occupy the catheter lumen, the portion distal of the most proximal hole will gradually be replaced by the patient's blood and end up creating the blood clot that blocks the catheter openings. Clot formation leads to reduced flow rates and may require intervention to clear the catheter.

By having all the openings of the annular lumen aligned in a single plane perpendicular to the axis of the lumen, the blood clot problem that blocks certain of the ports is avoided. In each of the embodiments shown, the infusion port set 22 are the only infusion ports from the annular lumen 24.

Indeed, whether the annular lumen is used for infusion or for aspiration, this co-planar alignment of openings avoids this blood clot limitation on the heparin lock function. Although the embodiments disclosed show that the annular lumen is the infusion lumen, it should be understood that the invention has equal value where the annular lumen is an aspiration lumen.

It is important that these co-planar openings face radially outward rather than face partially forward. The radially outward facing opening structure serves two purposes. First it minimizes recirculation of filtered blood from the infusion opening to the aspiration opening. Second, it assures a smoother surface to facilitate insertion of the catheter.

In summary, to provide the above advantages, the geometry of the openings have two important characteristics. A first is that the surface of the openings are substantially parallel to the axis of the catheter. The second is that the openings are all on a common plane near the end of the annular lumen; which common plane is substantially perpendicular to the axis of the catheter.

While the foregoing description and drawings represent the presently preferred embodiments of the invention, it should be understood that those skilled in the art will be able to make changes and modifications to those embodiments without departing from the teachings of the invention and the scope of the claims.

For example, the embodiment described employs a heparin solution to provide the fluid lock. Heparin is an anti-coagulant chemical and thus prevents blood clots. It should be understood that the structure of this invention could be employed with other fluids, including other anti-coagulants and antibiotics, to provide a fluid lock for anti-coagulant purposes or other purposes such as minimizing or avoiding infection. Solutions which could be used in lieu of heparin to provide a fluid lock include taurolidine, citrate taurolidine, antibiotic heparin, tentamicic citrate, citrate salts such as trisodium citrate dihydrate, warfarin and rT-PA. These are all constituents known in the art to perform known functions.

The fluid lock solution may also contain antibacterial, antimicrobial, or anticoagulant agents such as gentamicin, vancomycin, urokinase, sodium heparin, hirudin, EDTA, enoxaparin sodium, coumarin, indanedione derivative, anisindione, protamine sulfate, streptokinase and mixtures of these agents.

The fluid lock solution may also contain additional agents to enhance the viscosity of the citrate mixture, such as sorbitol and mannitol, polygeline, dextran, polyethylene glycol, glycerin, and mixtures thereof.

Additionally, parabens and photo-oxidants may also be added to the fluid lock solution.

In some circumstances a saline solution lock might be deemed sufficient to displace blood without requiring anticoagulant.

What is claimed is:

1. A method of maintaining a catheter fluid lock comprising:
providing an indwelling catheter having a proximal end and a distal end, wherein said catheter is adapted for use in the cardio-vascular system, said catheter having an annular lumen segment with an axis and a sole sidewall distal port arrangement that lies in a common plane, wherein said common plane is substantially perpendicular to said axis of said annular lumen segment, and wherein said annular lumen segment extends between said proximal end and said common plane, terminating substantially in said common plane,
implanting said catheter into a patient's cardio-vascular system,
injecting fluid into said annular lumen segment to fill said annular segment with said fluid, and
maintaining said fluid in said segment by virtue of said common perpendicular plane for said port arrangement.

2. The method of claim 1 wherein: said step of injecting fluid comprises injecting at least one of the fluids selected from the group consisting of anti-coagulant fluids, antibiotic fluids and saline.

3. The method of claim 1 wherein: each of said ports has an axis substantially perpendicular to said axis of said annular lumen.

4. The method of claim 1 wherein: said port arrangement is deployed along a major arc of the circumference of said annular lumen segment.

5. The method of claim 1 wherein: said distal port arrangement comprises a set of triangular ports nested against each other.

6. The method of claim 1 wherein: a set of radial ribs at the distal end of said annular lumen extending across said annular lumen defines a plurality of ports constituting said port arrangement.

7. The method of claim 1 wherein: said catheter comprises a second lumen, wherein said second lumen has a sidewall, and wherein said second lumen is coaxially surrounded by said annular lumen segment for at least a portion of the length of said second lumen.

8. The method of claim 7 wherein: said distal port arrangement is in part defined by segments of said annular sidewall, said sidewall segments extending between said ports and merging into said sidewall of said second lumen.

9. The method of claim 2 wherein: said port arrangement is deployed along a major arc of the circumference of said annular lumen segment.

10. The method of claim 2 wherein: said distal port arrangement comprises a set of triangular ports nested against each other.

11. The method of claim 2 wherein: said catheter comprises a second lumen, wherein said second lumen has a sidewall, and wherein said second lumen is coaxially surrounded by said annular lumen segment for at least a portion of the length of said second lumen.

12. The method of claim 11 wherein: said distal port arrangement is in part defined by segments of said annular sidewall, said sidewall segments extending between said ports and merging into said sidewall of said second lumen.

13. A catheter adapted to provide fluid lock comprising:
a shaft having a proximal end and a distal end, an aspiration lumen and an infusion lumen and adapted for indwelling use in the cardio-vascular system,
a first one of said lumens having a distal annular lumen segment deployed around the second one of said lumens, said annular lumen segment having an axis and an outer sidewall,
a distal port arrangement in said sidewall of said annular segment lying in a common plane intersecting each port of said port arrangement, said common plane being substantially perpendicular to said axis of said annular lumen segment, wherein said annular lumen segment extends between said proximal end and said common plane and terminates substantially in said common plane,
said port arrangement constituting the sole ports of said annular lumen segment, and wherein said catheter is configured to maintain a fluid in said annular lumen segment by virtue of said common plane for said port arrangement.

14. The catheter of claim 13 wherein: each of said ports has an axis substantially perpendicular to said axis of said annular lumen.

15. The catheter of claim 13 wherein: said ports are at the distal end of said annular lumen segment.

16. The catheter of claim 13 wherein: said port arrangement is deployed along a major arc of the circumference of said annular lumen segment.

17. The catheter of claim 13 further comprising: a set of radial ribs at the distal end of said annular lumen, said ribs extending across said annular lumen to define a plurality of ports constituting said port arrangement.

18. The catheter of claim 13 wherein: said second one of said lumens has a sidewall and wherein said distal port arrangement is in part defined by segments of said annular lumen outer sidewall, said annular sidewall segments extending between said ports and merging into said sidewall of said second one of said lumens.

19. The catheter of claim 13 wherein: said distal port arrangement comprises a set of triangular ports nested against each other.

20. The catheter of claim 14 wherein: said port arrangement is deployed along a major arc of the circumference of said annular lumen segment.

21. The catheter of claim 14 wherein: said second one of said lumens has a sidewall and wherein said distal port arrangement is in part defined by segments of said annular lumen outer sidewall, said annular sidewall segments extending between said ports and merging into said sidewall of said second one of said lumens.

22. The catheter of claim 14 wherein: said distal port arrangement comprises a set of nested triangular ports.

* * * * *